US012557843B2

(12) United States Patent
Larson

(10) Patent No.: US 12,557,843 B2
(45) Date of Patent: Feb. 24, 2026

(54) OTHER THAN CANNABINOIDS, FLAVONOIDS, AND TERPENES

(71) Applicant: Raymond Louis Larson, Aliso Viejo, CA (US)

(72) Inventor: Raymond Louis Larson, Aliso Viejo, CA (US)

(*) Notice: Subject to any disclaimer, the term of this patent is extended or adjusted under 35 U.S.C. 154(b) by 0 days.

(21) Appl. No.: 16/873,820

(22) Filed: Jul. 17, 2020

(65) Prior Publication Data

US 2025/0344763 A1 Nov. 13, 2025

Related U.S. Application Data

(60) Provisional application No. 63/100,380, filed on Mar. 11, 2020, provisional application No. 63/101,278, filed on Apr. 24, 2020.

(51) Int. Cl.
| | |
|---|---|
| *A61K 36/00* | (2006.01) |
| *A24F 40/10* | (2020.01) |
| *A24F 40/42* | (2020.01) |
| *A61K 31/05* | (2006.01) |
| *A61K 31/352* | (2006.01) |

(52) U.S. Cl.
CPC .............. *A24F 40/42* (2020.01); *A24F 40/10* (2020.01); *A61K 31/05* (2013.01); *A61K 31/352* (2013.01)

(58) Field of Classification Search
None
See application file for complete search history.

(56) References Cited

U.S. PATENT DOCUMENTS

| | | | | |
|---|---|---|---|---|
| 8,673,368 | B2 * | 3/2014 | Guy ....................... | A61K 36/00 424/725 |
| 10,568,865 | B2 * | 2/2020 | Levy .................... | A61K 31/065 |
| 2010/0168448 | A1 * | 7/2010 | Flockhart .................. | A61P 1/08 549/407 |
| 2014/0271940 | A1 * | 9/2014 | Wurzer ................ | A61K 36/185 424/725 |
| 2015/0182455 | A1 * | 7/2015 | Llamas ................. | C12C 11/003 435/161 |
| 2015/0352044 | A1 * | 12/2015 | Benson ................. | B65B 7/2842 206/205 |
| 2016/0243177 | A1 * | 8/2016 | Franklin .................. | A23L 27/10 |
| 2017/0231948 | A1 * | 8/2017 | Skuratovich ......... | A61K 9/0095 514/454 |
| 2017/0333503 | A1 * | 11/2017 | Ayres .................... | A61K 31/465 |
| 2017/0367386 | A1 * | 12/2017 | McElvany .............. | A23L 27/10 |
| 2018/0133272 | A1 * | 5/2018 | Crowley ................ | A61K 31/05 |
| 2018/0147179 | A1 * | 5/2018 | Raber .................. | A61K 9/1682 |
| 2019/0142034 | A1 * | 5/2019 | Forsythe ............... | A23L 33/105 426/590 |
| 2020/0281890 | A1 * | 9/2020 | Macnair .................. | A61P 25/20 |

FOREIGN PATENT DOCUMENTS

| | | | | | |
|---|---|---|---|---|---|
| CA | 3076929 | A1 | * | 3/2019 | .......... A61K 36/185 |
| KR | 20100011229 | A | * | 2/2010 | |
| WO | WO-2018175992 | A1 | * | 9/2018 | ............. A61K 47/18 |
| WO | WO 2019/100168 | | * | 5/2019 | |
| WO | WO-2019104442 | A1 | * | 6/2019 | ............... A23L 2/52 |

OTHER PUBLICATIONS

McLafferty(https://www.mentalfloss.com/article/56540/why-does-carbonation-make-drinks-taste-good) May 2014 (Year: 2014).*
Adventures in Homebrewing (https://blog.homebrewing.org/late-addition-malt-extract-late-addition-hops/#:~:text=To%20make%20the%20best%20use,the%20darkening%20of%20your%20beer.) Apr. 9, 2018 (Year: 2018) (Year: 2018).*
New Food Magazine (https://www.newfoodmagazine.com/article/15042/viscosity-measurements-food-products/) Oct. 27, 2014 (Year: 2014).*
New Food Magazine (https://www.newfoodmagazine.com/article/15042/viscosity-measurements-food-products/) snagit pic converted to pdf (Year: 2014).*
New Food Magazine (https://www.newfoodmagazine.com/article/15042/viscosity-measurements-food-products/) snagit pic converted to pdf additional page (Year: 2014).*
Piomelli and Russo (The Cannabis sativa Versus Cannabis indica Debate: An Interview with Ethan Russo, MD, Cannabis and Cannabinoid Research, vol. 1.1, 2016) (Year: 2016).*
Fundación Canna (https://www.fundacion-canna.es/en/flavonoids) retrieved on Apr. 2, 2024 (Year: 2015).*
Wayback machine reference date for Fundación Canna (https://www.fundacion-canna.es/en/flavonoids, retrieved on Apr. 2, 2024. Is used to show the reference date for the mentioned webpage. (Year: 2024).*
Fischedick (Identification of Terpenoid Chemotypes Among High (−)-trans-Δ9- Tetrahydrocannabinol-Producing *Cannabis sativa* L. Cultivars, Cannabis Cannabinoid Res. 2017; 2(1): 34-47), retrieved on Apr. 2, 2024. (Year: 2017).*
Romeyn (https://www.vogue.com/article/cannabis-terpene-cocktails-health-benefits) retrieved on Jul. 16, 2024, Aug. 9, 2017 (Year: 2017).*

* cited by examiner

*Primary Examiner* — Russell G Fiebig

(57) ABSTRACT

A pharmaceutical composition and administration apparatus includes a portable powered vaporizer with a mouthpiece, smokeless vaporizing element, and a removable chamber. The chamber contains a composition comprising tetrahydrocannabinol (THC), cannabidiol (CBD), FCC grade ethanol, flavoring, pharmaceutical grade nicotine, USP grade aqueous glycerine, USP/EP grade propylene glycol, and USP grade vegetable glycerine. In various formulas the THC may be at concentrations of 1-30%, 30-60% and 60-99%, while CBD concentrations may be 0-15% including other cannabinoids derived from extraction.

8 Claims, 2 Drawing Sheets

OTHER THAN CANNABINOIDS, FLAVONOIDS, AND TERPENES

This application benefits from U.S. provisional patent applications: 62/921,899, 63/100,380, 63/101,278. Priority is claimed to all of said applications, each of which is incorporated by reference herein in their entirety.

BACKGROUND

Marijuana plant varieties (*Cannabis setiva, Cannabis indica, Cannabis rederalis*, etc.) contain a variety of compounds, the major psychoactive compound being tetrahydrocannabinol (THC). Other compounds include a variety of additional cannabinoids, including cannabidiol (CBD), which is less psychoactive than THC and believed to have a wider scope of medical applications. Numerous publications report analgesic, antiemetic, and antiglaucomal effects, among others as resulting from CBD. While typically used recreationally, THC has also been shown to be an effective analgesic, antiemetic, and useful in treating nausea and attendant effects of cancer chemotherapy.

Administration of cannabinoids has evolved over time from the inhalation of marijuana combustion byproducts (i.e., smoking) to oral consumption of marijuana when combined with foods, or the oral consumption of cannabinoid compounds (such as THC and other cannabinoids) in extracted pill form. Additionally, transdermal patches, as discussed in U.S. Pat. No. 6,503,532 have been developed and used in the art. These methods of administration are disfavored however.

When inhaling combustion byproducts, users cannot regulate the percentage of individual cannabinoids entering the lungs. Additionally, undesirable irritating, and potentially toxic or carcinogenic are produced and inhaled as well. The use of orally consumed products such as pills allows users to adjust the quantity of a given cannabinoid ingested, but is disfavored due to the delay of cannabinoid effects caused by the digestive system. Additionally, many marijuana users prefer the mimicry of smoking conferred by inhalation for personal and social reasons. While a transdermal patch may be an effective way of time-releasing a known quantity of particular cannabinoids into the blood stream, this method suffers from drawbacks similar to orally ingested pills, including a lack of social interaction.

For these reasons, there is a need for a cannabinoid composition possessing a predetermined quantity of THC and CBD (in addition to other cannabinoids) for users to obtain a desired recreational, medical or combined effect. There is also a need for an administration technique that allows users to control the quantity of cannabinoids administered through an inhalation apparatus that avoids simple combustion.

SUMMARY

Presented is a formulation of cannabinoid and a smokeless administration of use through vaporization in a portable and rechargeable delivery system. The cannabinoids are mixed with several vegetable glycerols including propylene glycol, among other components. Several cannabinoid formulations with varying levels of THC and CBD are contemplated, and preferably will be contained in a cartridge. In this manner, cartridges can be interchangeable with other cartridges depending on a desired effect.

Two embodiments of cartridges are contemplated, a disposable cartridge and a refillable cartridge. In the instance of a refillable cartridge, a syringe may accompany the delivery system for refilling the cartridge. This is due to the high viscosity of high THC/CBD percentage formulations and the attendant difficulty of transferring them from a source vessel into a refillable cartridge.

BRIEF DESCRIPTION OF THE FIGURES

FIG. 5 shows chemical formula for Tetrahydrocannabinol.

FIG. 6 shows the chemical formula for Cannabidiol.

DESCRIPTION

Figure 1:
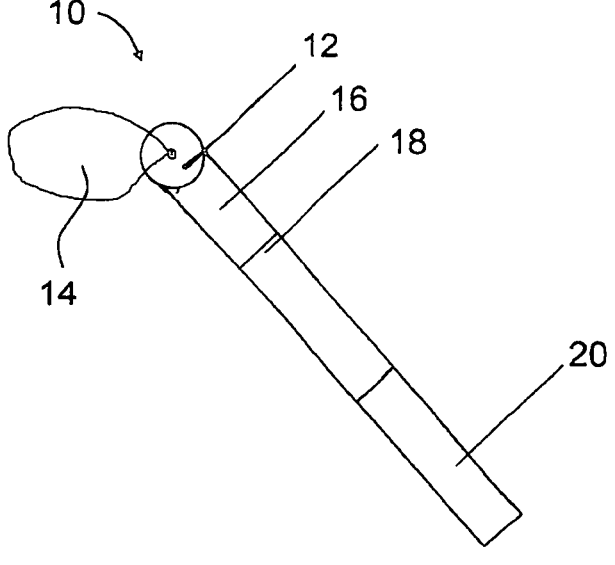
FIG. 1 shows a disposable smokeless "e-cigarette" type vaporizing apparatus.

An improved pharmaceutical composition and administration apparatus is disclosed. The administration apparatus comprising a portable powered vaporizing apparatus having a mouthpiece, a smokeless vaporizing element, and a removable chamber. Portable vaporizers of this variety are typically known as e-cigarettes, which have a heating element for vaporizing nicotine and nicotine-containing oils. In the embodiments disclosed herein, a heating element calibrated for the use cannabinoids is contemplated.

When prepared for use, the chamber contains a cannabinoid composition comprising tetrahydrocannabinol (THC), cannabidiol (CBD), FCC grade ethanol, flavoring, pharmaceutical grade nicotine, USP grade aqueous glycerine, USP/EP grade propylene glycol, and USP grade vegetable glycerine.

Preferably a food grade ethanol and flavoring is used in the composition. Additionally, in one preferred embodiment, the nicotine may include USP grade nicotine extract, and may be extracted from organic sources. Prior to manufacturing In one preferred embodiment the food grade glycerin will comprise a 99.7% USP Grade Glycerine having 99.70% Glycerol content, 0.3% maximum moisture content, 10 ppm max chlorides, 10 max (APHA) coloring, a minimum specific gravity of 1.2612, 20 ppm max, 5 ppm max heavy metals, 30 ppm max chlorinated compounds, I 00 ppm max residue on ignition, 1.000% max fatty acid and esters, 0.5% water, and assayed at between 99.0 to 101.0% (on a dry basis). Additionally the food grade glycerine passes tests for DEG and related compounds and organic volatile impurities. In another embodiment pure vegetable glycerin may be used.

Preferably the propylene glycol selected for usage will be pharmaceutical grade propylene glycol with a specified purity greater than 99.8%, and in compliance with United States Pharmacopeia (USP), European Pharmacopeia (EP), Japanese Pharmacopeia (JP) and Food Chemical Codex (FCC) standards.

Several formulas are contemplated when formulating the pharmaceutical composition. In all cases, where 0% is listed, it is understood that any amount under the maximum percentage down to greater than 0% is intended, including trace amounts. A first formula includes a 30% THC:

0% to 30% Tetrahydrocannabinol (THC)

0% to 15% Remaining cannabinoids including cannabidiol (CBD)

0% to 20% FCC grade ethanol
0% to 04% Food grade flavoring
0% to 03% Pharmaceutical grade nicotine
0% to 20% USP grade acqueous glycerine
0% to 70% USP/EP grade propylene glycol
0% to 25% USP grade vegetable glycerine A second formula combines known cannabinoids THC and CBD at specific concentrations:

0% to 30% Tetrahydrocannabinol (THC)
0% to 15% Cannabidiol (CBD)
0% to 15% Remaining cannabinoids excluding cannabidiol (CBD)
0% to 20% FCC grade ethanol
0% to 04% Food grade flavoring
0% to 03% Pharmaceutical grade nicotine
0% to 20% USP grade acqueous glycerine
0% to 70% USP/EP grade propylene glycol
0% to 25% USP grade vegetable glycerine A third formula combines employs a greater percentage of THC along with other known cannabinoids including cannabidiol at a lower percentage, and reduced percentages of acqueous glycerine and propylene glycol:

30% to 60% Tetrahydrocannabinol (THC)
0% to 15% Remaining cannabinoids including cannabidiol CBD)
0% to 20% FCC grade ethanol
0% to 04% Food grade flavoring
0% to 03% Pharmaceutical grade nicotine
0% to 10% USP grade acqueous glycerine
0% to 60% USP/EP grade propylene glycol
0% to 25% USP grade vegetable glycerine A fourth formula comprises the higher percentage of THC but with a known quantity of CBD in addition to remaining cannabinoids. As with the previous formula, the acqueous glycerine and propylene glycol are reduced, but in this case including the USP vegetable grade glycerine as well.

30% to 60% Tetrahydrocannabinol THC)
15% to 30% Cannabidiol (CBD)
0% to 15% Remaining cannabinoids excluding cannabidiol (CBD)
0% to 20% FCC grade ethanol
0% to 04% Food grade flavoring
0% to 03% Pharmaceutical grade nicotine
0% to 10% USP grade acqueous glycerine
0% to 60% USP/EP grade propylene glycol
0% to 15% USP grade vegetable glycerine A fifth formula comprises the maximum percentage of THC. With this formula, it is intended that either replaceable cartridges or a syringe will be used due to the higher viscosity of the pharmaceutical composition. Additionally, in this formulation, a much reduced quantity of acqueous glycerine, propylene glycol and vegetable glycerine is used:

60% to 99% Tetrahydrocannabinol (THC)
0% to 10% Remaining cannabinoids including cannabidiol (CBD)
0% to 20% FCC grade ethanol
0% to 04% Food grade flavoring
0% to 03% Pharmaceutical grade nicotine
0% to 10% USP grade acqueous glycerine
0% to 40% USP/EP grade propylene glycol
0% to 10% USP grade vegetable glycerine The sixth formula adds a known quantity of CBD to the high concentration of THC in the formula. Due to the high percentage of THC and CBD, the remaining cannabinoids are reduced as well as the acqueous glycerine, propylene glycol and vegetable glycerine:

60% to 99% Tetrahydrocannabinol THC)
0% to 15% Cannabidiol (CBD)

0% to 10% Remaining cannabinoids including cannabidiol (CBD)
0% to 20% FCC grade ethanol
0% to 04% Food grade flavoring
0% to 03% Pharmaceutical grade nicotine
0% to 10% USP grade acqueous glycerine
0% to 40% USP/EP grade propylene glycol
0% to 10% USP grade vegetable glycerine In all embodiments it is preferable to have an administration apparatus that is a vaporizer having a mouth piece, a chamber for holding a quantity of the pharmaceutical composition, and a battery powered heating element. A preferable administration apparatus may include an "e-cigarette" type apparatus in which a battery powered heating element is combined with a chamber for holding a preferred cannabinoid formulation. The cannabinoid formulation is drawn from the chamber and heated by the heating element to a vaporization temperature at which point the vapors are inhaled in by a user.

Referring to FIG. 1, one common type of preferred and inexpensive administration apparatus is a onetime use only disposable e-cigarette vaporizer 10. The disposable e-cigarette vaporizer 10 includes a mouthpiece 12 for extracting vaporized cannabinoids 14, the mouthpiece 12 is in fluid communication with an atomizer 16 which combines vaporized cannabinoids 14 with air drawn through the disposable e-cigarette vaporizer 10. The atomizer 16 is powered by a battery 18 adapted to power the atomizer 16 sufficiently to vaporize a quantity of cannabinoids housed in a chamber 20 in fluid communication with the atomizer 16. In this embodiment, once the chamber 20 is empty or the battery 18 dies, the entire apparatus is discarded.

Figure 2:
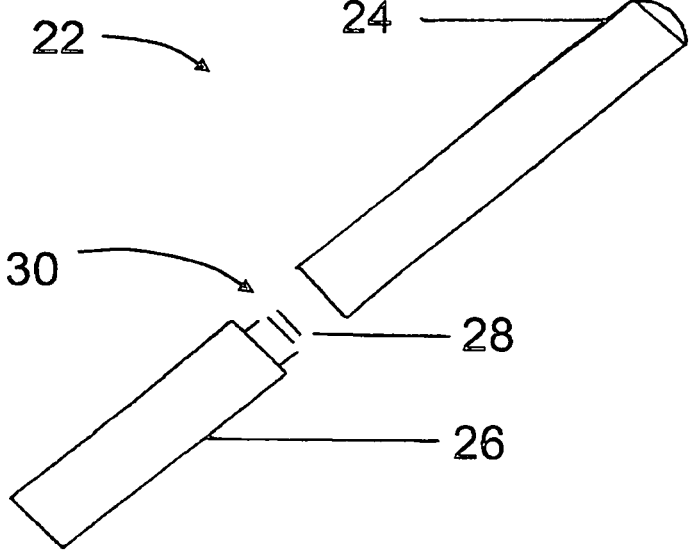
FIG. 2 shows a smokeless "e-cigarette" type vaporizing apparatus having a disposable cartridge.

Referring to FIG. 2, a second type of preferred administration apparatus includes a replaceable cartridge vaporizer 22. The replaceable cartridge vaporizer 22 includes a battery 24. A chamber 26 and atomizer 28 are connectable to the battery 24 using a threaded connection 30. In this manner, the chamber 26 may be replaceable once a quantity of cannabinoid formula housed in the chamber 26 is exhausted. This apparatus may be preferable since the battery 24 is capable of vaporizing a quantity of cannabinoid formula in multiple chambers.

Figure 3:
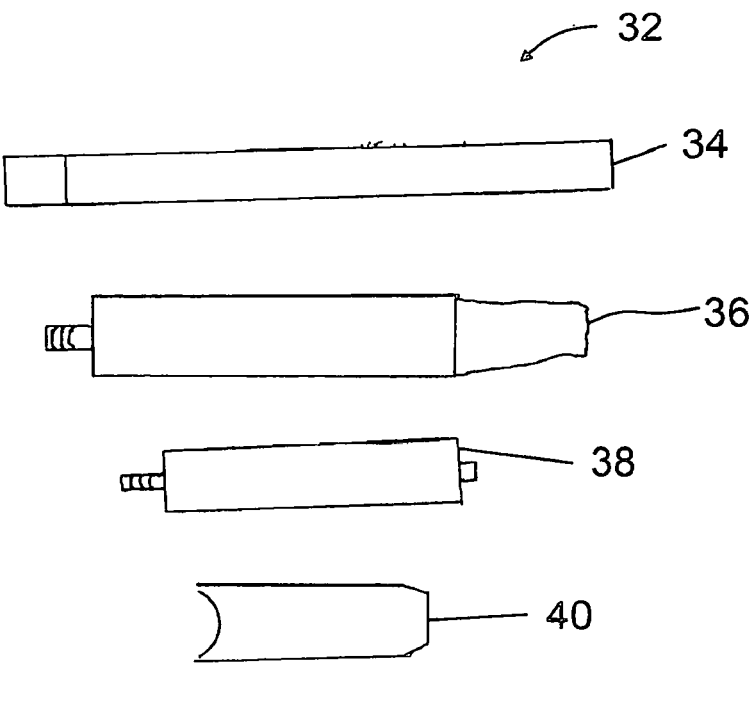
FIG. 3 shows a disassembled smokeless "e-cigarette" type vaporizing apparatus having a refillable cartridge.

Referring to FIG. 3, a third type of preferred administration apparatus is a commonly used e-cigarette vaporizer 32. In this embodiment the components of the e-cigarette vaporizer 32 may be disassembled into a battery 34, either a disposable cartridge 36 or refillable cartridge 38, and a mouthpiece 40. The battery 34 is preferably combined with an atomizer (not shown). Also, in instances where a disposable cartridge 36 is used, the disposable cartridge 36 may have a mouthpiece incorporated therein.

Figure 4:
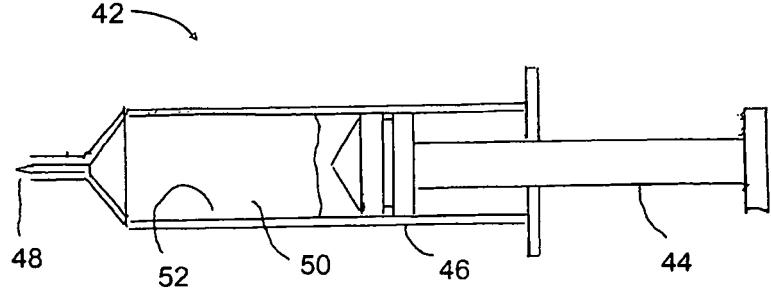
FIG. 4 shows a syringe used to refill the cartridge of a refillable "e-cigarette" type vaporizing apparatus.

Referring to FIG. 4, in certain instances, where a refillable cartridge 36 is used, the cannabinoid formulation may be to viscous for easy decanting into a refillable cartridge 36. In such an instance, a syringe 42 may be employed. It is anticipated that a typical syringe having a plunger 44, barrel 46 and needle 48 will be used, although the needle may be adapted and sized for an efficient union with the refillable cartridge 36 (FIG. 3). While the syringe 42 may be used to take up a cannabinoid mixture 50 into the barrel interior 52, it is also anticipated that syringes may be produced and purchased pre-loaded with a cannabinoid mixture 50, ready for introduction into an empty cartridge 36. In this manner cartridges may be easily and effectively refilled with a desired cannabinoid formulation.

When properly administered, the pharmaceutical composition of the present invention may be useful for both recreational and medical purposes. Medical uses may include, but are not limited to, treating pain, nausea, loss of appetite (particularly nausea associated with chemotherapy in cancer treatments), glaucoma, arthritis, dementia, multiple sclerosis, and for deterring weight loss.

While the apparatus and associated formulas have been described in detail with reference to specific embodiments thereof, it will be apparent to one skilled in the art that various changes and modifications can be made therein without departing from the spirit and scope thereof. Thus, it is intended that the present description cover the modifications and variations of the invention provided they come within the scope of the appended claims and their equivalents.

In this invention it is imperative regarding the avoidance and/or exclusion of both: THC and CBD. However this invention as a formulary includes:

ALL other cannabinoids, except and specifically CBD & THC as the 2 excluded cannabinoids. Currently, well over a hundred noted cannabinoids have been discovered in Cannabis/Hemp.

This invention is relative to ALL infused products currently known and also those not yet innovated that can be for all living bodies: humans, pets, mammals, etc. for consumption. Some delivery examples of this provisional formulary given yet not limited to: edibles, skin care, essential oil mixtures, sublingual & spray forms, pills, bath and body lotions, shampoo, topically, IV, inhalation, nasal delivery, suppository, beverages (Coffee/tea/water/beer/alcohol, etc.) whether in low or high viscous forms. The estimated sufficient rage I feel would be accommodating is greater than zero (0)% and up to 20% by weight.

Some examples, perhaps, would be:

1) Greater than zero (0)% by wet. to 20% wt. cannabinoids excluding CBD.

2) Greater than (0)% by wt. to 20% by wt. other than THC and CBD in a cannabinoid formulary.

3) ALL cannabinoids except for THC and CBD in an essential oil formulary.

Basically, any and all other cannabinoid formulas/inventions found to contain THC and or CBD however with this provisional filing/invention, THC and/or CBD are specifically excluded.

Terpene formulas and flavonoid formulas will be excluding CBD and/or THC. Terpenes, Flavonoids, and Cannabinoids in all formulations from all 3 lists: A, B, and C can be one or more ingredients taken from any of the mentioned or added lists. Formulas maybe excluding one or more of: A, B, C to any one formula such as Myrcene & CBD and/or THC. Formulas maybe also be excluding Flavonoids and/or CBD, THC in % of Terpenes from greater than zero (0) to 30%. Formulas may have synthetic or any other plant Terpene or Flavonoid included.

This invention is relative to ALL infused products currently known and also those not yet innovated that can be for all living bodies, humans, pets, mammals, etc. for consumption. Some delivery examples of this provisional formulary given yet not limited to edibles, skin care, essential oil mixtures, sublingual & spray forms, pills bath and body lotions, shampoo, topically, IV inhalation, nasal delivery, suppository, beverages (coffee/tea/water/beer/alcohol, etc.) whether in low or high viscous forms. The estimated sufficient range I feel would be accommodating is greater than zero (0)% and up to 20% by weight.

Example of Formulary:

0%-30% wt THC and 30%-60% wt THC or 60%-99% wt THC

0%-15% wt CBD

One or more of remaining cannabinoids greater than 0% wt to 20% wt chosen from the C list, excluding cannabidiol (CBD) and/or THC Greater than 0% wt to 15% wt of the C list and a terpene from list A other than CBD and/or THC and myrcene 0% wt-20% FCC ethanol or alcohol 0% wt-5% wt Food Grade Flavoring 0% wt-5% wt Pharmaceutical grade nicotine 0% wt-25% USP grade aqueous glycerin 0% wt-40% wt USP/EP grade glycol 0% wt-60% wt USP grade vegetable glycerin 0% wt-70% wt coconut oil 0% wt-70% wt essential oils 0% wt-15% wt terpenes 0% wt-15% wt flavonoids 15% wt-30% wt CBD 30% wt-60% wt CBD 1% wt-30% wt selected item(s) on list(s)

1% wt-30% wt selected terpene(s)Iflavonoids

This invention deals with compositions using NO THC (Tetrahydrocannabinol). There is only one symbol, as shown in FIG. 5, that exits in the chemistry world. You don't have to be a person skilled in the art to see the difference. A person skilled in the art can see by using NO CBD compound symbol, as shown in FIG. 6, in any part of the formula.

Sample 1: A liquid composition: 1.5% wt-15% wt Cannabinoids other than THC, CBD, and Trace-3% Nicotine.

Exhibit-B shows THC and CBD separated. We show some of the other Cannabinoids together a person skilled in the art can see the different things the other Cannabinoids do on their own. This is not a 103 issue.

Exhibit-B1 shows only THC and CBD.

Exhibit B-2 shows NO THC and/or CBD.

Sample 2: A liquid composition 1.1% wt.-15% wt. Cannabinoids OTHER THAN, THC and/or CBD Sample 3: A liquid composition trace-15% Cannabinoids other than THC and/or CBD This invention presents several formulations with most of them using OTHER TIIAN THC and CBD. Within the formula(s), the inventor has added or subtracted percentages of cannabis related compounds. Example: CBN % wt. 0% wt-50% wt. This is an example of one of the cannabinoids of which will be used. Besides cannabinoids, Terpenes, Flavonoids, and other plant based matter including also synthetics.

Formulas will include: Water, Carbonated Water, Water Soluble matter, Hops, Ethanol, Virtually All Beverages, Nicotine infused pills/cough drops, Beer, Wine, and any new or newly discovered infusible ideas.

This invention uses ALL 3 of the compounds: Cannabinoids, Terpenes, Flavonoids other than THC and CBD for ALL 3 categories. Oral and topical will be also used. Also used will be virtually all consumables like, Beverages. Also, skin care products The use of pills and other delivery methods used in this invention. There are over 100 cannabinoids discovered thus far, however there are many undiscovered drugs that are still undiscovered thus, will be formulated. The amounts of OTHER THAN THC and CBD are very low in Cannabis (Marijuana and Hemp). I am targeting to increase or decrease the amount of each compound including Flavonoids and Terpenes. With the high cost of these rare (OTHER THAN THC/CBD) compounds in each plant like CBN for instance today is $25,000 per Kilo VS steel at $6.00 per Kilo. Some formulas may EXCLUDE one or more of ALL cannabinoids, Flavonoids, and Terpenes.

Below is a list of possible ingredients that can be included in the present invention:

1) 0% wt.-95% wt. Water Soluble
2) 0% wt.-35% wt. Hops
3) 0% wt.-95% wt. Carbonated Water
4) 0% wt.-98% wt. Water
5) 0% wt.-35% wt. Malts
6) 0% wt.-20% wt. Electrolytes
7) 0% wt.-10% wt. Caffeine
8) 0% wt.-20% wt. Melatonin
9) 0% wt.-30% wt. THC
10) 30% wt.-60% wt. THC
11) 60% wt.-99% wt. THC
12) 0% wt.-30% wt. CBD
13) 30% wt.-60'% wt. CBD
14) 60% wt.-99% wt. CBD
15) 0% wt.-20% wt. Remaining Cannabinoids Excluding CBD
16) 0% wt.-30% wt. FCC grade ethanol
17) 0% wt.-4% wt. Food grade flavoring
18) 0% wt.-5% wt Nicotine
19) 0% wt.-80% wt. USP aqueous glycerin
20) 0% wt-80% wt. USP/EP grade propylene glycol
21) 0% wt.-80% wt. USP grade vegetable glycerin
22) 0% wt.-30% wt. Cannabinoids and/or Flavonoids and/or Terpenes Other than any individual compositions.

List A, Terpenes

This article will set out two types of secondary metabolites that are biosynthesised by the plant *Cannabis sativa* L. and probably produce synergy with the effects cannabinoids.

It is being observed that cannabinoids are not the only active substances in the Cannabis plant. Certain studies showed that there were differences between the effects produced by pure cannabinoids and the ones caused by the plant, although cannabinoids are administered in equal doses in both cases. These observations point to the existence of other active substances in the Cannabis plant, which have an intrinsic pharmacological action and/or can modify the pharmacological action of cannabinoids. Two groups of active substances have been identified presently; terpenes and flavonoids, both of which appear in sufficient concentrations to have pharmacological activity. From a scientific perspective, neither which kind of specific compounds are capable of producing synergy with cannabinoids, nor how they are formed, have been proven. Both terpenes and flavonoids are under the increasing attention of the scientific and medical community due to their proven pharmacological actions. In the following paragraphs, we will try to show the current state of the studies about the biological and synergistic activity between these active substances and the cannabinoids.

Terpenes

Terpenes are volatile organic compounds formed by the union of hydrocarbon of 5 carbon atoms, known as isoprene. The smallest and most volatile compounds are monoterpenes, which are biosynthesised by the union of two isoprene molecules. The biggest and least volatile are biosynthesised by the union of three or more isoprene molecules. The sesquiterpenes are next in the chain, which are formed by the union of three isoprene molecules. Terpenes are secondary metabolites, which provide the plant with its organoleptic characteristics (aroma and flavour) and that constitutes most of the essential oil produced by aromatic plants.

Terpenes and cannabinoids share their biosynthetic pathways and, in fact, cannabinoids are terpeno-fenolic compounds. In the Cannabis plant, terpenes also share the biosynthesis and accumulation spaces. Thus, both types of compounds are biosynthesised in the glandular trichomes of leaves and flowers and are accumulated in large proportions in the exuded resin. In any case, it seems that certain non-capitular glandular trichomes, which are more abundant in leaves surface, are specialised in synthesising terpenes. It has been shown that the ratio between monoterpenes and sesquiterpenes in leaves and flowers is rather different. This is due to the dominance of sessile trichomes in leaves, which are more specialised in synthesising terpenes, while capitate trichomes are more abundant in flowers and are specialised in the synthesis of monoterpenes and cannabinoids. The proportion of terpenes in the plant is normally less than 1%, potentially achieving up to 10% of the resin composition.

Terpenes have different functions in plants. The two main ones are the protection against insects and herbivorous animals, as well as protection against high temperatures. Plants react by producing terpenes in the areas affected through the action of insects and herbivorous animals, which act as bitter compounds that repel them or even as pesticides in some cases. Monoterpenes, which are more volatile, dominate in inflorescences to repel insects. Sesquiterpenes, which are more bitter, are more abundant on leaves acting against herbivorous animals. Some terpenes can act as a decoy in some plants, attracting either pollinating insects or predatory ones that feed on herbivorous insects, which are beneficial for the plant. As plants sense a temperature rise, they begin synthesising more terpenes and under high temperatures during night or day, more terpenes are released. Terpenes evaporate at high temperatures, producing airflows that cool the plant and lessen transpiration, preventing the plant from drainage. In the Cannabis plant, terpenes are exuded in the resin and confer it with the sticky and viscous quality that will get some insects trapped and immobilised, thus, acting as a protection against insects and high temperatures. Hence, it is easy to observe that Cannabis plants smell stronger during the first morning hours than during the warmest part of the day as a large amount of terpenes evaporate. This is the reason why it is recommended harvesting the mature plants during the first morning hours, in order to get the maximum production of essential oil.

Cannabis essential oil is mainly formed by a high proportion of monoterpenes and a variable proportion of sesquiterpene. Such proportions, together with the extraction performance, will be mainly affected by the degree of drying that Cannabis achieves when processed for the extraction of the essential oil. In fact, the extraction performance of the essential oil by steam distillation of the fresh plant is lower than 1%, with a composition of 80-90% in monoterpenes and 10-20% in sesquiterpenes. However, it will be around 0.1% in the dried plant and its composition will be lower in monoterpenes, where it can reach 50% in sesquiterpenes, due to the fact that monoterpenes are very volatile and evaporate quickly during the plant drying process. Usually, the essential oil obtained from industrial hemp, which contains many leaves and it is normally processed dried, is chiefly formed by sesquiterpenes. Some sesquiterpenes remain in the plant even after a 15 minute decarboxilation treatment at 120° C. This is the case for cariofileno, which has a moist soil aroma characteristic of baked or cooked Cannabis. Likewise, the evaporation of monoterpenes during the drying process is responsible for the transformation of the aroma from the fresh plant to a well-dried one, although the change in taste comes from the degradation of chlorophylls. Thus, fresh plants have minty, citric, fruity, etc. aromas that soften when dried.

Nevertheless, terpenes are not just responsible of the aroma, but they also have an important biological and therapeutic activity. It has been scientifically shown that the essential oils of plants have therapeutic properties and are the pharmacological base of aromatherapy. These oils and pure terpenes can also be used as flavourings in the food industry, as they are non-toxic compounds. The therapeutic properties will specifically depend on the terpene in question.

The most abundant terpenes in the Cannabis plant that form most of its essential oil are the monoterpenes myrcene, pinene, limonene, linalool, eucalyptol and sesquiterpene caryophyllene. The variation in the ratio between these terpenes is what produces the wide range of aromas that can be found in the Cannabis plant. It has been recently discovered that they can also take part in the varied pharmacologic effects caused by Cannabis, as well as generate synergy with cannabinoids.

Myrcene

Myrcene, or β-myrcene, is a lineal monoterpene carbohydrate and is the main component of the essential oil of wild thyme, comprising 40% of its overall composition. It is found at high concentrations in other plants such as hop, mango and limoncillo, among others. Myrcene acts as an anti-inflammatory interfering in the prostaglandins' metabolic pathway. Myrcene is the sedative active ingredient of the hop, which is used in herbalism and in natural therapies to help with sleeping disorders.

Studies on laboratory animals have shown myrcene's sedative, hypnotic, analgesic and muscle relaxant properties. Its mechanism of action has not been totally unveiled yet, but it could be that it has adrenergic and/or opioid effects, as the analgesic effect is blocked by an antagonistic opioid (naloxone). It has also been shown that the myrcene alters the blood-brain barrier, favouring the penetration of cannabinoids in the brain and increasing the effects.

In a recent study, it was shown that analysing the composition of terpenes in *indica* varieties against *sativa* varieties, a greater presence of myrceno was found in *indica* varieties; up to 60%-80% of their composition. It has been accepted that *indica* varieties are more relaxing and sedative than *sativa* varieties. Bringing together all the evidence, we can speculate that the effect of myrceno combined with THC can be highly physical and hypnotic, which is common in *indica* varieties.

Pinene

Pinene is the common name of two isomer bicyclic monoterpenoids, α-pinene, β-pinene, which are main components of the pine resin and of other conifers, which gives it the name, although it is also the terpene most widely distributed in nature. In fact, it is not only found in the plant kingdom, as the two compounds are part of the chemical communication system of insects and also act as insect repellent.

These components have significant antibiotic effects, even against antibiotic resistant pathogens. Another therapeutic activities attributed to them is that of anti-inflammatories, blocking the inflammatory signal of prostagladins in a similar way to myrcene. They also act as bronchodilator in humans when they are inhaled in low concentrations. This effect could produce a larger absorption of cannabinoids when smoking or when vaporizing Cannabis with a product rich in alpha and beta pineno, which would increase plasma concentrations and, subsequently, the cannabinoids effect.

A-pinene is an acetylcholinesterase inhibitor that may be beneficial for memory and may reduce the negative THC effects on it, although this is no more than a mere assumption at this point. A-pineno has also served as biosynthetic base for the ligands of the cannabinoid receptor CB2. Pineno seems to be quite balanced within the different *Cannabis* varieties representing around the 10% of the terpenes group and not exceeding 15-20%.

Limonene

Limonene is a cyclic carbohydrate and a main component of the essential oil of lemons and other citrus fruits, which is where its name comes from. It is also the second most widely distributed terpene in nature and it is an intermediate product in other terpenes' biosynthesis. In contrast with pinene, limonene is not found in insects, yet it still has some repellent and insecticide effects. It is widely used in the food and pharmaceutical industries as flavouring. Recent research has been carried out to look at its usefulness in formulations of dermal patches, to improve the transdermal absorption of other active substances.

Limonene is used in cosmetics and household cleaning product industries as a fragrance and as a biodegradable, organic and environmentally friendly solvent. It is quickly absorbed by inhalation or by the skin and it is metabolised quickly, however there are indications it can accumulate in fatty tissues, such as brain tissue. Limonene is not toxic, nor does it cause skin irritation, yet some of its products, which are oxidised by contact with air, provoke skin and mucous irritation. This lead to 3% of people exposed to high doses for a long period of time, such as the workers of the paint industry, suffering from dermatitis. Nonetheless, limomene has therapeutic effects in certain diseases and some antiseptic properties, mainly against the bacteria responsible for acne.

Studies on laboratory animals suggest that limonene has anxiolytic effects, causing a rise of serotonin and dopamine neurotransmitters in the brain. It has been shown that the dispersal of limonene in the environment has produced a decrease in the depressive symptoms of hospital patients in addition to a strong immunostimulation. Linonene also produces apoptosis, also called cell death, in breast cancer cells. Its effectiveness is being tested in clinical trials. In addition to this, the use of limomeno against gastroesophageal reflux has been patented.

Linalool

Linalool is a lineal monoterpene alcohol resulting from the main substances of the essential oil of lavender, but it is also found in many other plants. It is widely used as fragrance in cleaning and hygiene products, as an intermediate product in the chemical industry and as insecticide against flies and cockroaches, however it is not useful as an insect repellent. The essential oil of lavender eases skin burns and can even reduce the morphine intake needed, when inhaled by patients with post-operative treatment. These effects are attributed to linalool for being the main component of the essential oil of lavender, as after its ingestion, other substances for example the monoterpene linalyl acetate, hydrolyses into linalool. Linalool in itself has shown to have anxiolytic effects on a comparable level to local anaesthetics such as lidocaine or menthol. It also demonstrates analgesic effects in laboratory animals when mediated by adenosine A2A and glutamate receptors, as well as sedative effects by inhalation.

In addition to these effects, linalool has anti-seizure properties that inhibit glutamatergic activity and is also able to decrease the release of neurotransmitters of the neurons under glutamate stimulation. In this way, we could argue that the sedative, anxiolytic and anti-seizure effects have their mechanism of action based on the modulation of the glutamate and GABA neurotransmitters, similarly to the way the cannabinoides act. Thus, a Cannabis plant with both THC and linalool will probably produce a significant sedative and analgesic effect, due to the synergy between the two compounds. However, a Cannabis plant with CBD and/or THCV and/or CBDV and linalool will probably produce a synergistic effect as an anti-seizure medication, which would be useful in cases of epilepsy, even as a preventive measure.

Eucalyptol

Eucalyptol, also known as 1,8-cineol, is a monoterpene ester that makes up almost the totality of the essential oil of eucalyptus, from which it gets its name, but it is also widely distributed in the plant kingdom. It acts as an insect repellent and insecticide, although it is produced by certain orchids to attract bees. Eucalyptol is used as food additive to add flavour. Products containing eucalyptol need to have less than 0,002% of it, as the intake of greater amounts can affect the central nervous system (CNS) and might even be psychotropic. Eucalyptol is widely used in the cosmetic and chemical industries, but it is still classified as a toxin that might have a negative influence on reproduction. Some researches have shown certain clinical efficacy of eucalyptol for treating asthma and sinusitis, as well as being an anti-inflammatory and a local analgesic.

Furthermore, it has been shown to have immunosuppressive and in vitro anti-leukaemia properties. In the aforementioned study about terpenes profiles in different varieties of *Cannabis*, it was found that eucalyptol, carene, phellandrene and terpinolene are terpenes found almost exclusively in *sativa* varieties. Eucalyptol, carene and felandrene are found in proportions close to 5%, whereas terpinolene was around 20% of the total in *sativa* varieties, while they will not go over 1% in *indica* varieties. Eucalyptol is the only one of these compounds that has been shown to be active in the CNS, which is almost unique to *sativa* varieties and that such varieties have a euphoriant effect different from *indica* varieties. From this we can hypothesise that the synergy between THC and eucalyptol is what makes a difference regarding the qualitative difference of the activating effect of *sativa* varieties. That being said, the myrcene could also be responsible for the hypnotic effect of *indica* varieties.

Caryophyllene

Caryophyllene is what we call the mixture of three compounds: α-caryophyllene or humulene, β-caryophyllene, which is the main component of the essential oil of black pepper, and caryophyllene oxide, a result of the oxidation of both melissa and eucalyptus. All of them are bicyclic sesquiterpenic carbohydrate and are present in all *Cannabis* varieties. In fact, caryophyllene oxide is the signal detected by sniffer dogs trained to find Cannabis. We have to bear in mind that it is one of the less volatile terpenes and that, as mentioned earlier, it resists the process of decarboxylation, thus becoming the terpene most easily found in Cannabis extracts. In the plant kingdom, β-caryophyllene plays an evolutive survivalism role by increasing its release and biosynthesis in plants parasitised by herbivorous insects, so it will attract other predatory insects to reduce the damage produced by herbivores. Caryophyllene oxide takes part in the defence system of the plants, functioning as an insecticide and an antifungal. It should be noted that both caryophyllene and CBC join in the defence against fungi attacks. Moreover, caryophyllene oxide has shown a clinic effectiveness against certain cases of fungal infection. B-caryophyllene, has anti-inflammatory properties and operates at two levels, one is the blocking of the prostaglandins' inflammatory pathway, as happens with myrcene and pinene, and the other is as CB2 cannabinoid receptor agonist.

This last mode of action makes β-caryophyllene the first non-cannabinoid molecule with cannabinomimetic functioning, which is also authorised for human consumption and thus open to a wide therapeutic applicability. Its anti-inflammatory and analgesic effects, as well as its effectiveness in the treatment of atypical dermatitis in animal models has been proven, although not yet in humans. Due to its effects on the prostaglandins inflammatory pathway, caryophyllene also has anticoagulant properties and unexpected gastric protection effects. Gastric ulcers are a secondary effect of certain anti-inflammatory prostaglandins antagonists, which limit their therapeutic effectiveness, however, caryophyllene does not only have this secondary effect, but it can also act as protection against their appearance.

| Terpene analysis utilizing Gas Chromatography-Flame ionization Detection (GC-FID) | | | |
|---|---|---|---|
| | mg/g | % | LOD/LOQ mg/g |
| α Pinene | 0.716 | 0.076 | 0.044/0.135 |
| Camphene | <LOQ | <LOQ | 0.053/0.16 |
| Sabinene | ND | ND | 0.054/0.165 |
| β Pinene | 0.453 | 0.0456 | 0.054/0.162 |
| Myrcene | 5.126 | 0.1526 | 0.054/0.164 |
| α Phellandrene | ND | ND | 0.073/0.222 |
| 3 Carene | ND | ND | 0.057/0.174 |
| α Terpinene | ND | ND | 0.06/0.18 |
| Limonene | 1.422 | 0.1422 | 0.026/0.078 |
| Eucalyptol | ND | ND | 0.042/0.126 |
| Ocimene | 2.259 | 0.2259 | 0.056/0.171 |
| γ Terpinene | ND | ND | 0.06/0.181 |
| Sabinene Hydrate | ND | ND | 0.036/0.108 |
| Fenchone | ND | ND | 0.061/0.184 |
| Terpinolene | ND | ND | 0.045/0.135 |
| Linalool | 0.631 | 0.0631 | 0.038/0.116 |
| Fenchol | 0.255 | 0.0255 | 9.045/0.138 |
| (−)-Isopulegol | ND | ND | 0.026/0.08 |
| Camphor | ND | ND | 0.108/0.327 |
| Isoborneol | ND | ND | 0.066/9.201 |
| Borneol | <LOQ | <LOQ | 0.097/0.293 |
| Menthol | ND | ND | 0.044/0.135 |
| Terpineol | 0.205 | 0.0205 | 0.045/0.436 |
| Nerol | ND | ND | 0.045/0.137 |
| R-(+)-Pulegone | ND | ND | 0.045/0.135 |
| Geraniol | ND | ND | 0.033/0.1 |
| Geranyl Acetate | ND | ND | 0.031/0.095 |
| α Cedrene | ND | ND | 0.034/0.102 |
| β Caryophyllene | 2.279 | 0.2279 | 0.036/0.108 |
| α Humulene | 0.783 | 0.0783 | 0.025/0.076 |
| Valencene | 0.067 | 0.0067 | 0.015/0.046 |
| Nerolidol | ND | ND | 0.07/0.212 |
| Caryophyllene Oxide | <LOQ | <LOQ | 0.055/0.167 |
| Guaiol | ND | ND | 0.044/0.132 |
| Cedrol | ND | ND | 0.057/0.173 |
| α Bisabolol | 0.729 | 0.0729 | 0.034/0.102 |
| Total Terpene Concentration: | 14.928 | 1.4928 | |

List B Flavonoids

Everything You Need to Know about Cannabis Flavonoids Like Cannabinoids and Terpenes, they Contribute a Range of Effects.

Flavonoids are a group of phytonutrients most remarkably known for providing vivid non-green color pigments to the plant kingdom—think blue in blueberries, red in roses, the purple in your Grandaddy Purp. Alongside cannabinoids like THC and CBD, and terpenes like myrcene and limonene, flavonoids in cannabis also produce a range of effects. Commonly grouped together, flavonoids combine with each other and other cannabis phytonutrients to play a highly bioactive role in both the plant's consumption and cultivation.

As cannabis grows, various flavonoids are expressed, operating in areas of plant-growth like UV light filtering and pest and fungi deterrence. When we consume cannabis, those same flavonoids contribute to the color, taste, smell, entourage effect, and overall sensory experience. While contributing a wide variety of health benefits to the cannabis plant itself during cultivation, flavonoids also have a great reputation among the wellness community for providing a range of health benefits to humans.

Although understudied in the cannabis plant due to federal prohibition, flavonoids are one of the largest nutrient families known to scientists. Over 6,000 unique flavonoids have been identified in research studies. Many of these flavonoids are found in the edible plants we eat and cook everyday, like vegetables, fruits, and herbs. Of all the plant kingdom, common edible foods can be especially nutrient-rich in flavonoids, especially when grown properly. With more researchers studying cannabis every day, new findings show the cannabis plant can also be a flavonoid-rich resource, kicking it right up there with our broccoli and mashed potatoes. Consider "catechins," a type of flavonoid found in green tea and cacao. Researched extensively, catechins are known to provide antioxidant and cardiovascular health benefits, and also produce favorable effects on cholesterol levels in humans. Another flavonoid, "quercetin," a nutrient readily present in many fruits and vegetables, as well as cannabis, is known for having potent antioxidant and antiviral properties. Sometimes flavonoid names are fairly easy to deduce, basing them by the name of the food in which they're increasingly present, like "tangeretin," found in tangerines and most citrus fruit. Some, like kaempferol, luteolin, and quercetin, naturally occur across a variety of plants, but flavonoids truly unique to the cannabis plant are now referred to as "cannaflavins."

Research is underway to distinguish cannaflavins from more common flavonoids. For example, it was recently discovered that cannabis flavonoid "cannaflavin-A" inhibits "PGE-2," a prostaglandin responsible for inflammation known for responding well to nonsteroidal anti-inflammatory drugs (NSAIDs) like aspirin. The study showed that cannaflavin-A reduces inflammation and is exponentially more powerful than aspirin.

Cannflavin-B and cannflavin-C are being studied, too, while researchers are still learning how the presence of more common flavonoids in cannabis like β-sitosterol, vitexin, isovitexin, apigenin, kaempferol, quercetin, luteolin, and orientin work in conjunction—with or resistance to—cannabis cannabinoids and terpenes.

Because many flavonoids have high antioxidant properties that support the detoxification of tissue-damaging molecules, flavonoid consumption is often—although not always—associated with a decreased risk of certain cancers, most notably lung and breast cancer. Still today, more research is required on flavonoids' role in these specific conditions.

While the distribution of flavonoids in the cannabis plant varies on genetics, growing conditions, and the flavonoid itself, the compounds are found readily in cured cannabis leaves and flowers, reaching concentrations large enough for us to enjoy them. Soon, through extractions, or possibly synthesis, we might be twaxing joints with a dab of terp oil and a ribbon of "flav" oil.

More research is required to fully understand flavonoids in cannabis, but what we know is this: In addition to their contribution to cannabis plant growth and the human sensory experience, there are numerous benefits to be gained from their consumption—just like the flavonoids in our food.

Flavonoids

Flavonoids are secondary polyphenolic metabolites that commonly have a ketone group and yellowish pigments, after which they are named (from the Latin flavus, "yellow"). Flavonoids can be divided in four main groups: flavonoids, isoflavonoids, neoflavonoids and anthocyanins. Nevertheless, for the sake of simplicity, we will refer to them all with the common term of flavonoids.

Flavonoid biosynthesis follows the phenylpropane metabolic pathway, in which the cumaril-SCoA is formed from the aminoacid known as phenylalanine, which is mixed together with the malonil-CoA form a group of substances known as chalcones. These are the backbone of every flavonoid and anthocyanin's biosynthesis.

This reaction is catalyzed by the chalcone synthase enzyme, which belongs to the family of the polyketide synthases (PKS). This PKS family also contains olivetol synthase, responsible for the synthesis of cannabinoids.

Flavonoids cover o wide range of functions in plants, although they mainly act as yellow pigments in petals and leaves to attract pollinating insects. They might also appear as bluish pigments (anthocyanins) to receive certain wavelengths of light, which permits the plant to be aware of the photoperiod. Many of these flavonoids also protect the plant by being involved in the filtering of ultraviolet light. On a cellular level, flavonoids act as regulators of the cellular cycle. Some of them are synthesised in the plant's roots and have crucial roles in establishing symbiotic fungi or mycorrhyzas, while at the same time they fight the infections caused by pathogenic fungi.

Flavonoids have relevant pharmacological activities on 'in vitro' models, such as: antioxidant, anti-inflammatory, antiallergic, antibiotic, antidiarrheal and against cancer. It has not been possible to prove an antioxidant activity on 'in vivo' models, just as it has not been possible to relate it to any effectiveness against cancer. Some studies seem to indicate that a diet rich in flavonoids can diminish the risk of cancer, but there are no significant statistics regarding this claim.

We can find different types of flavonoids in the Cannabis plant, such as: cannflavine A, cannfiavine B, cannflavine C, vitexin, isovitexin, apigenin, kaempferol, quercetin, luteolin and orientin. The distribution of these in the plant, varies depending on the type of flavonoid, but none have been found in the root system of the Cannabis plant. The total content of flavonoids in the Cannabis' leaves and flowers can reach 2.5% of its dry weight, while it is almost non existent in seeds and roots. Some studies suggest that the distribution and concentration of flavonoids in the Cannabis plant can be useful from a chemical and taxonomic point of view. The following is a brief description on the therapeutic properties of these flavonoids. Most of these compounds are soluble in water, which could explain certain therapeutic effects of the herbal infusions and the decoctions in Cannabis water, as the cannabinoids are partly soluble in water.

Flavonols of Broccoli: Qercetin, Kaemferol, Myricetin, Galangin, Fisetin,

Flavones of Skullcap: Aplgenin, Chyrsin, Luteolin, Baicalin, Balcalein

Flavonols of Green tea: Catechins, Epicatechin, Epigallocatechin, Epicatechin, Gallate Cannflavins A, B and C They have anti-inflammatory activity due to the fact that they inhibit the prostaglandins' inflammatory pathway. This mechanism is shared with other terpenoids which are present in the Cannabis plant, providing a better synergy and anti-inflammatory effect to that coming from cannabinoids.

Vitexin and Isovitexin

Therapeutic applicability for gout, inhibiting the thyroid peroxidase.

Kaempferol

It seems to have an antidepressant effect. A rich diet in kaempferol may reduce the risk of cancer and some coronary diseases. Although some are opposed, other theories state that Cannabis seems to have certain antidepressant effects in some cases, so it could be that there is a synergistic effect coming from the combination of kaempferol and cannabinoids.

Apigenin

It has shown to decrease the secondary effects of ciclosporin A, an immunosuppressive administered during organ transplants to avoid the rejection of the transplanted organ. It has also been proven that apigenin is one of the few substances capable of stimulating the monoamine transporter, altering the neurotransmitter levels. It has recently become clear that apigenin acts as an anxiolytic and sedative on the GABA receptors. The fact that this effect is shared by the cannabinoids bring us to a possible synergy between axiolict and sedative effects of cannabinoids.

Flavanones of Grapefruit: Eriodictyol, Hseperitin, Naringenin

Anthocyanidins of Pomegranate: Cyanidin, Pelagronidin, Delphinidin, Peonidin, Malvidin Isoflavonoids of Soybeans: Genistein, Daidzein, Glyctein, Formononetin Quercitin It inhibits viral enzymes and it can have antiviral effects. It also inhibits the production of prostaglandins, acting as an anti-inflammatory. The quercitin can have synergy with the cannabinoids too by increasing the anti-inflammatory effects. A recent study suggests quercitin may have therapeutic applicability in treating fibromyalgia, due to its anti-inflammatory effects. As has been shown, Cannabis has therapeutic effects in managing fibromyalgia, which could prove the synergy between quercitin and Cannabis. Similarly, quercitin inhibits the monoamine oxidase enzyme (MAO), which is involved in the metabolism of neurotransmitters and pharmaceuticals. This factor should be to be taken into account, with regards to possible interactions with particular pharmaceuticals.

Luteonin and Orientin (Luteonin Glucoside)

Both luteonin and orientin have shown to have pharmacologic effects as antioxidants, anti-inflammatories, antibiotics and as agents against cancer in preclinical studies. They can also have synergy with cannabinoids.

In this article, we have verified that there are other types of active substances in the Cannabis plant, and that the effects of this plant could clearly be influenced by the possible synergy between the effects of cannabinoids, terpenes and flavonoids. Therefore, the anti-inflammatory effect of the Cannabis plant could be most affected by a probable synergy, due to the fact that the three groups of compounds converge in similar or complementary mechanisms of action.

LIST C Cannabinoids

Cannabigerol-type (CBG)

Cannabigerol
(E)-CBG-C5

Cannabigerol monomethyl ether
(E)-CBGM-C5 A

Cannabinerolic acid A
(Z)-CBGA-C5 A

Cannabigerovarin
(E)-CBGV-C3

Cannabigerolic acid A
(E)-CBGA-C5 A

LIST C Cannabinoids

Cannabigerolic acid A
monomethyl ether
(E)-CBGAM-C₅ A

Cannabigerovarinic acid A
(E)-CBGVA-C₃ A

Cannabichromene-type (CBC)

Cannabichromene
CBC-C₅

(±)-Cannabichromenic acid A
CBCA-C₅ A (±)-Cannabivarichromene,
(±)-Cannabichromevarin
CBCV-C₃

LIST C Cannabinoids (±)-Cannabichromevarinic acid A
CBCVA-C₃ A

Cannabidiol-type (CBD)

(−)-Cannabidiol
CBD-C₅

Cannabidiol momomethyl ether
CBDM-C₅

Cannabidiol-C₄
CBD-C₄

(−)-Cannabidivarin
CBDV-C₃

19

-continued

LIST C Cannabinoids

Cannabidiorcol
CBD-C$_1$

Cannabidiolic acid
CBDA-C$_5$

Cannabidivarinic acid
CBDVA-C$_3$

Cannabinodiol-type (CBND)

Cannabinodiol
CBND-C$_5$

Cannabinodivarin
CBND-C$_3$

20

-continued

LIST C Cannabinoids

Tetrahydrocannabinol-type (THC)

$\Delta^9$-Tetrahydrocannabinol
$\Delta^9$-THC-C$_5$ $\Delta^9$-Tetrahydrocannabinol-C$_4$
$\Delta^9$-THC-C$_4$ $\Delta^9$-Tetrahydrocannabivarin
$\Delta^9$-THCV-C$_3$ $\Delta^9$-Tetrahydrocannabiorcol
$\Delta^9$-THCO-C$_1$ $\Delta^9$-Tetrahydrocannabinolic acid A
$\Delta^9$-THCA-C$_5$ A -continued -continued LIST C Cannabinoids LIST C Cannabinoids $\Delta^9$-Tetrahydrocannabinolic acid B
$\Delta^9$-THCA-C$_5$ B (−)-$\Delta^8$-trans-(6aR,10aR)-Tetrahydrocannabinolic acid A
$\Delta^8$-THCA-C$_5$ A $\Delta^9$-Tetrahydro-cannabinolic acid-C$_4$ A and/or B
$\Delta^9$-THCA-C$_4$ A and/or B (−)-(6aS,10aR)-$\Delta^9$-Tetrahydrocannabinol
(−)-cis-$\Delta^9$-THC-C$_5$ Cannabinol-type (CBN)

$\Delta^9$-Tetrahydrocannabivarinic acid A
$\Delta^9$-THCVA-C$_3$ A

Cannabinol
CBN-C$_5$ $\Delta^9$-Tetrahydrocannabiorcolic acid A and/or B
$\Delta^9$-THCOA-C$_1$ A and/or B Cannabinol-C$_4$
CBN-C$_4$ (−)-$\Delta^8$-trans-(6aR,10a)-$\Delta^8$-Tetrahydrocannabinol
$\Delta^8$-THC-C$_5$ Cannabivarin
CBN-C$_3$ -continued -continued LIST C Cannabinoids LIST C Cannabinoids Cannabinol-C$_2$
CBN-C$_2$ (+)-(9S,10S)-Cannabitriol
(+)-trans-CBT-C$_5$ Cannabiorcol
CBN-C$_1$

*and (S,R)*

(±)-(9R,10S/9S,10R)-Cannabitriol
(±)-cis-CBT-C$_5$

Cannabinolic acid A
CBNA-C$_5$ A (−)-(9R,10R)trans-10-O-Ethyl-cannabitriol
(−)-trans-CBT-OEt-C$_5$ Cannabinol methyl ether
CBNM-C$_5$

*and (S,S)*

(±)-(9R,10R/9S,10S)-Cannabitriol-C$_3$
(±)-trans-CBT-C$_3$

Cannabitriol-type (CBT)

(−)-(9R,10R)-trans-Cannabitriol
(−)-trans-CBT-C$_5$ 8,9-Dihydroxy-$\Delta^{6a(10a)}$-tetrahydrocannabinol
8,9-Di-OH- -continued LIST C Cannabinoids Cannabidiolicacid A
cannabitriol (−)-(6aR,9S,10S,10aR)-9,10-Dihydroxy-
hexahydrocannabinol, Cannabiripsol
Cannabiripsol-C$_5$ (−)-6a,7,10a-Trihydroxy-Δ$^9$-tetrahydrocannabinol 10-Oxo-Δ$^{6a(10a)}$-
tetrahydrocannabinol
OTHC

I claim:

1. A composition of cannabinoids, terpenes, flavonoids comprising:
   (a) Greater than 0% wt.-30% wt. of at least two Tetrahy-drocan-type (THC), of at least one +Cannabitriol-type (CBT), of at least two +Cannabigerol-type (CBG), of at least two +Cannabichromene-type (CBC), of at least two Cannabiabinol-type (CBN) selected from a group consisting of: CBN-C$_2$, CBD-C$_4$, CBCV-C$_3$, CBND-C$_5$, CBND-C$_3$, CBN-C$_1$, CBN-C$_5$, CBD-C$_1$, CBDV-C$_3$, CBCC$_5$, CBDA-C$_5$, CBDM-C$_5$, CBO-C$_5$, CBDM-C$_5$, CBNMC$_5$, CBT-C$_5$, (E)-CBG-C$_5$, (E)-CBGM-C$_5$A, (Z)-CBG$_5$A, (E)-CBGV-C$_3$, (E)-CBGA-C$_5$A, (E)-CBGAM-C$_5$A, (E)-CBGVA-C$_3$A, Delta-9-THC- C$_5$, Delta-9-THC-C$_4$, Delta-9-THCO-C$_1$, Delta-9-THCV-C$_3$, Delta-9-THCA-C$_5$A, Delta-9-THCA-C$_5$B, OTHC, CBG, CBN and CBC; and
   (b) Greater than 0% wt.-30% wt. of at least twelve terpenes/Flavonoids selected from the group consisting of: fisetin, chrysin, baicalein, naringenin, epicatechin, pelargonidin, malvidin, sabinene hydrate, (−)-isospulegol, isoborneol, nerol, r-(+)-pulegone, geranyl acetate, fenchol, cedrol, myrcene, limonene, linalool, a pinene, fenchol, borneol, terpineol, menthol and 3Carene;
wherein the composition is a beverage, and
wherein the cannabinoids are soluble in carbonated water.

2. The composition of claim 1, further comprising:
   0% wt.-30% wt. alcohol;
   0% wt.-35% wt. Hops; and
   wherein the at least twelve terpenes/Flavonoids are selected from the group consisting of: fisetin, chrysin, baicalein, naringenin, epicatechin, pelargonidin, mal-vidin, myrcene, limonene, a pine, nerol, cedrol, fren-chone, methol, terpineol, borneol and glycitein.

3. The composition of claim 1, further comprising:
   Greater than 0% wt-30% wt. of four terpenes/Flavonoids are selected from the group consisting of: sabinene hydrate, isoborneol, nerol, r-(+)-pulegone, geranyl acetate, and cedrol;
   0% wt.-30% wt. alcohol;
   0% wt.-35% wt. Hops; and
   0% wt. cannabinoids.

4. The composition of claim 1, further comprising:
   1% wt.-30% wt. of five terpenes/flavonoids selected from the group consisting of: sabinene hydrate, (−)-isospulegol, isoborneol, nerol, r-(+)-pulegone, geranyl acetate, fenchol, cedrol, and linolool;
0% wt.-30% wt. alcohol;
0% wt.-35% wt. Hops; and
0% wt. cannabinoids.

5. The composition of claim 1, further comprising:
   1% wt.-30% wt. of at least three additional terpenes/Flavonoids selected from the group consisting of: sabinene hydrate, (−)-isospulegol, isoborneol, nerol, r-(+)-pulegone, geranyl acetate, fenchol, limonene and linolool.

6. The composition of claim 1, further comprising:
   1% wt.-30% wt. of at least 10 terpenes/flavonoids selected from the group consisting of: fisetin, chrysin, baicalein, naringenin, epicatechin, pelargonidin, myrcene, limo-nene, menthol, borneol, apinens, nerol, linalool and glycitein; and
wherein combination of the cannabinoids (a) is other than cannabigerol-type (CBG) and the Remaining eight can-nabinoids greater than 0%-15% wt.

7. The composition of claim 1, further comprising
   1% wt-30% wt. of at least terpenes/Flavonoids selected from the group consisting of: sabinene hydrate, isobor-neol, nerol, r-(+)-pulegone, geranyl acetate, fenchol, cedrol; myrcene, methol, borneol, limonene, linalool, a pinen, fisetin, chrysin, baicalein, naringenin, epicat-echin, pelargonidin, malvidin and glycitein;
0% wt.-30% wt. alcohol; and
0% wt.-35% wt. Hops.

8. The composition of claim 1, further comprising:
   0% wt.-30% wt. alcohol;
   0% wt.-35% wt. Hops;
   1% wt.-30% wt. of at least ten terpenes/Flavonoids are selected from the group consisting of: sabinene hydrate, (−)-isospulegol, isoborneol, nerol, r-(+)-pulegone, geranyl acetate, myrcene, terpineol, fenchol, cedrol, fisetin, chrysin, baicalein, naringenin, epicatechin, pelargonidin, malvidin, and glycitein; and wherein the combination of cannabinoids (a) are other than THC and the remaining Tetrahydrocan-type all nine cannabinoids greater than 1%-30% wt.

* * * * *